US008137972B2

(12) United States Patent
Laurencin et al.

(10) Patent No.: US 8,137,972 B2
(45) Date of Patent: Mar. 20, 2012

(54) BIOCOMPATIBLE, BIODEGRADABLE POLYMER-BASED, LIGHTER THAN OR LIGHT AS WATER SCAFFOLDS FOR TISSUE ENGINEERING AND METHODS FOR PREPARATION AND USE THEREOF

(75) Inventors: Cato T. Laurencin, Elkins Park, PA (US); Solomon R. Pollack, North Wales, PA (US); Elliot Levine, Cherry Hill, NJ (US); Edward Botchwey, Philadelphia, PA (US); Helen H. Lu, New York, NY (US); Mohammed Yusuf Khan, Philadelphia, PA (US)

(73) Assignees: Drexel University, Philadelphia, PA (US); The Wistar Institute, Philadelphia, PA (US); The Trustees Of The University of Pennsylvania, Philadelphia, PA (US)

( * ) Notice: Subject to any disclaimer, the term of this patent is extended or adjusted under 35 U.S.C. 154(b) by 1155 days.

(21) Appl. No.: 11/755,254

(22) Filed: May 30, 2007

(65) Prior Publication Data
US 2007/0231900 A1 Oct. 4, 2007

Related U.S. Application Data

(63) Continuation of application No. 10/052,121, filed on Jan. 17, 2002, now abandoned.

(60) Provisional application No. 60/262,128, filed on Jan. 17, 2001.

(51) Int. Cl.
| | |
|---|---|
| C12N 5/00 | (2006.01) |
| C12N 5/02 | (2006.01) |
| C12N 5/07 | (2010.01) |
| C12N 11/08 | (2006.01) |
| C12N 11/04 | (2006.01) |
| A61F 2/00 | (2006.01) |

(52) U.S. Cl. ....... 435/396; 424/423; 424/93.7; 435/180; 435/182; 435/325

(58) Field of Classification Search .................. None
See application file for complete search history.

(56) References Cited

U.S. PATENT DOCUMENTS

| | | | | |
|---|---|---|---|---|
| 4,448,884 | A | 5/1984 | Henderson | 435/402 |
| 5,006,467 | A | 4/1991 | Kusano et al. | 435/180 |
| 5,866,155 | A * | 2/1999 | Laurencin et al. | 424/425 |
| 6,001,643 | A | 12/1999 | Spaulding | 435/298.2 |
| 6,210,715 | B1 | 4/2001 | Starling et al. | 424/489 |
| 6,328,990 | B1 * | 12/2001 | Ducheyne et al. | 424/426 |

OTHER PUBLICATIONS

Becker et al., "Three-Dimensional Growth and Differentiation of Ovarian Tumor Cell Line in High Aspect Rotating-Wall Vessel: Morphologic and Embryologic Considerations", *J. Cellular Biochem.* 1993 51(3):283-289.

Burwell R.G. Bone Grafts, Derivatives and Substitutes., M.R. Urist and R.G. Burwell, Editors 1994, Butterworth-Heinemann Ltd.: Oxford.
Casser-Bette et al., "Bone Formation by Osteoblast-Like Cells in a Three-Dimensional Cell Culture", *Calcified Tissue International* 1990 46:46-56.
Cook et al., "The Effect of Recombinant Human Osteogenic Protein-1 on Healing of Large Segmental Bone Defects" *J. Bone Joint Surg. Am.* 1994 76(6):827-838.
Devin et al., "Three-dimensional degradable porous polymer-ceramic matrices for use in bone repair", *J. Biomater. Science-Polymer Edition* 1996 7(8):661-669.
Ducheyne et al., "Effect of Bioactive Glass Templates on Osteoblast Proliferation and In Vitro Synthesis of Bone-Like Tissue", *J. Cell. Biochem.* 1994 56:162-167.
El-Ghannam et al., "Bioactive material template for in vitro synthesis of bone" *J. Biomed. Mater. Res.* 1995 29:359-370.
Gadzag et al., "Alternatives to Autogenous Bone Graft: Efficacy and Indications", *J. Amer. Acad. Ortho. Surg.* 1995 3(1):1-8.
Goldstein et al., "Effect of Osteoblastic Culture Conditions on the Structure of Poly(DL-Lactic-co-Glycolic Acid) Foam Scaffolds", *Tissue Engineering* 1999 5(5):421-433.
Granet et al., "Rotating-wall vessels, promising bioreactors for osteoblastic cell culture:comparison with other 3D conditions", *Cell Eng.* 1998 3:513-519.
Ishaug et al., "Bone formation by three-dimensional stromal osteoblast culture in biodegradable polymer scaffolds", *J. Biomed. Mater. Res.* 1997 36:17-28.
Ishaug-Riley et al., Three-dimensional culture of rat calvarial osteoblasts in porous biodegradable polymers, *Biomaterials* 1998 19:1405-1412.
Klement and Spooler, "Utilization of Microgravity Bioreactors for Differentiation of Mammalian Skeletal Tissue", *J. Cellular Biochem.* 1993 51:252-256.
Labarca and Paigen, "A Simple, Rapid, and Sensitive DNA Assay Procedure", *Anal. Biochem.* 1980 102:344-352.
Langer and Vacanti, "Tissue Engineering", *Science* 1993 260(5110):920-926.
Laurencin et al., "Tissue Engineered Bone-Regeneration Using Degradable Polymers:The Formation of Mineralized Matrices", *Bone* 1996 19(1):93S-99S.
Laurencin et al., "A highly porous 3-dimensional polyphosphazene polymer matrix for skeletal tissue regeneration", *J. Biomed. Mater. Res.* 1996 30:133-138.
Lewis et al., "Use of Microgravity Bioreactors for Development of an In Vitro Rat Salivary Gland Cell Culture Model", *J. Cellular Biochem.* 1993 51:265-273.
Masi et al., "Adhesion, Growth, and Matrix Production by Osteoblasts on Collagen Substrata", *Calcified Tissue International* 1992 51:202-212.
Mizuno et al., Osteogenesis by Bone Marrow Stromal Cells Maintained on Type I Collagen Matrix Gels In Vivo, *Bone* 1997 20(2):101-107.

(Continued)

*Primary Examiner* — David Naff
(74) *Attorney, Agent, or Firm* — Woodcock Washburn, LLP

(57) ABSTRACT

Scaffolds for tissue engineering prepared from biocompatible, biodegradable polymer-based, lighter than or light as water microcarriers and designed for cell culturing in vitro in a rotating bioreactor are provided. Methods for preparation and use of these scaffolds as tissue engineering devices are also provided.

19 Claims, No Drawings

OTHER PUBLICATIONS

Prewett et al., "Three-Dimensional Modeling of T-24 Human Bladder Carcinoma Cell Line: A New Simulated Microgravity Culture Vessel", *J. Tissue Culture Methods* 1993 15:29-36.

Qui et al., "Formation and Differentiation of Three-Dimensional Rat Marrow Stromal Cell Culture on Microcarriers in a Rotating-Wall Vessel", *Tissue Engineering* 1998 4(1):19-34.

Rattner et al., "Characterization of Human Osteoblastic Cells:Influence of the Culture Conditions", *In Vitro Cellular & Developmental Biology-Animal* 1997 33:757-762.

Stanford et al., "Rapidly Forming Apatitic Mineral in an Osteoblastic Cell Line (UMR 106-01 BSP)", *J. Biol. Chem.* 1995 270(16):9420-9428.

Thomson et al., "Hydroxyapatite fiber reinforced poly($\alpha$-hydroxy ester) forms for bone regeneration", *Biomaterials* 1998 19:1935-1943.

Van Belle H., "Kinetics and Inhibition of Alkaline Phosphatases from Canine Tissues", *Biochimica et Biophysica Acta* 1972 289:158-168.

Wu and Forsling, "Potentiometric and Spectrophotometric Study of Calcium and Alizarin Red S. Complexation", *Acta Chemica Scandinavica* 1992 46:418-422.

Crotts et al., Journal of Controlled Release. vol. 35, 1995, pp. 91-105.

* cited by examiner

BIOCOMPATIBLE, BIODEGRADABLE POLYMER-BASED, LIGHTER THAN OR LIGHT AS WATER SCAFFOLDS FOR TISSUE ENGINEERING AND METHODS FOR PREPARATION AND USE THEREOF

This patent application is a continuation of U.S. patent application Ser. No. 10/052,121 filed Jan. 17, 2002 now abandoned which claims the benefit of priority from U.S. Provisional Application Ser. No. 60/262,128 filed Jan. 17, 2001, teachings of each of which are hereby incorporated by reference in their entirety.

This invention was supported in part by funds from the U.S. government (NASA Grant No. NAG 9-832 and NIH Grant No. AR07132-23) and the U.S. government has certain rights in the invention.

FIELD OF THE INVENTION

The present invention relates to scaffolds for tissue engineering specifically designed for cell culture in vitro in a rotating bioreactor. Scaffolds of the present invention comprise biocompatible, biodegradable polymer-based microcarriers which are lighter than and/or light as water. In a preferred embodiment, the biocompatible, biodegradable, lighter than or light as water microcarriers are bonded into a scaffold which is then cultured with cells in a rotating bioreactor. Methods for preparation and use of these scaffolds as tissue engineering devices are also provided.

BACKGROUND OF THE INVENTION

In 1993, Langer and Vacanti et al. estimated the number of bone repair procedures performed in the United States at over 800,000 per year (Science 1993 260(5110):920-926). Today, skeletal reconstruction has become an increasingly common and important procedure for the orthopaedic surgeon. Conventional approaches in bone repair have involved biological grafts such as autogenous bone or autografts, allogenic bone or allografts and xenografts (Burwell, R. G. History of bone grafting and bone substitutes with special reference to osteogenic induction, in Bon Grafts, Derivatives and Substitutes., M. R. Urist and R. G. Burwell, Editors. 1994, Butterworth-Heinemann Ltd.: Oxford. p. 3). Currently, autograft is the preferred biological graft most often utilized in the clinical setting, having success rates as high as 80-90% and no risk of immune rejection or disease transfer (Cook et al. J. Bone Joint Surg. Am. 1994 76(6):827). However, due to limited availability of autografts and risks of donor site morbidity, alternative approaches to bone repair have been sought.

Numerous tissue engineering solutions have been proposed to address the need for new bone graft substitutes.

One potentially successful repair solution seeks to mimic the success of autografts by removing cells from the patient by biopsy and growing sufficient quantities of mineralized tissue in vitro on implantable, three-dimensional scaffolds for use as a functionally equivalent autogenous bone tissue. In this way, an ideal bony repair environment is created by reproducing the intrinsic properties of autogenous bone material, which include: a porous, three-dimensional architecture allowing osteoblast, osteoprogenitor cell migration and graft re-vascularization; the ability to be incorporated into the surrounding host bone and to continue the normal bone remodeling processes; and the delivery of bone forming cells and osteogenic growth factors to accelerate healing and differentiation of local osteoprogenitor cells (Burwell, R. G. History of bone grafting and bone substitutes with special reference to osteogenic induction, in Bone Grafts, Derivatives and Substitutes., M. R. Urist and R. G. Burwell, Editors. 1994, Butterworth-Heinemann Ltd.: 5 Oxford, p. 3; Gadzag et al. J. Amer. Acad. Ortho. Surg. 1995 3 (1): 1).

Biodegradable scaffolds for in vitro bone engineering, which possess a suitable three-dimensional environment for the cell function together with the capacity for gradual resorption and replacement by host bone tissue have also been described. See, e.g. Casse-bette et al. Calcified Tissue International 1990 46(1):46-56; Masi et al. Calcified Tissue International 1992 51(3):202-212; Rattner et al. In Vitro Cellular & Developmental Biology-Animal 1997 33(10):757-762; Mizuno et al. Bone 1997 20(2):101-107; El-Ghannam et al. J. Biomed. Mater. Res. 1995 29(3):359-370; Ducheyne et al. J. Cell. Biochem. 1994 56(2):162-167; Ishaug et al. J. Biomed. Mater. Res. 1997 36(1):17-28; Ishuag-Riley et al. Biomaterials 20 1998 19(15):1405-1412; Goldstein et al. Tissue Engineering 1999 5 (5): 421-433; Devin et al. J. Biomater. Science-Polymer Edition 1996 7(8):661-669; Laurencin et al. Bone 1996 19(1):593-599; Thomson et al. Biomaterials 1998 19(21):1935-1943; and Laurencin et al. J. Biomed. Mater. 2 5 Res. 1996 30(2):133-138. This three-dimensional matrix milieu provides the necessary microenvironment for cell-cell and cell-matrix interaction, and is sufficient for the production of limited amounts of mineralized bone matrix in static culture. To demonstrate clinical feasibility of tissue engineered bone and to sufficiently match the intrinsic properties of autogenous bone graft material, however, rapid mineralization of osteoid tissue grown in vitro must be achieved. In the above-described three-dimensional matrices, nonhomogeneous cell seeding 35 confines cell density to the near surface of the scaffold and mineralized tissue formation is limited by inadequate diffusion of oxygen, nutrients, and waste.

Using porous polylactic glycolic acid (PLAGA) foams with pore sizes ranging from 150 to 710 µm, Ishaug-Riley et al. (Biomaterials 1998 19(15):1405-1412) have observed a limit to osseous tissue ingrowth and mineralization in a static culture environment of about 200 µm. While it is possible that structures with larger pores would facilitate greater diffusion, important cell-cell interactions and scaffold mechanical integrity could be compromised.

Formation of three-dimensional assemblies for culturing of various cell types in a rotating bioreactor have been described. See e.g. Goldstein et al. Tissue Engineering 1999 5(5):421-433; Granet et al. Cell Eng. 1998 36(4):513-519; Klement et al. J. Cellular Biochem. 1993 51(3):252-256; Qui et al. Tissue Engineering 1998 4(1):19-34; Lewis et al. J. Cellular Biochem. 1993 51(3):265-273; Becker et al. J. Cellular Biochem. 1993 51(3):283-289; and Prewett et al. J. Tissue Culture Methods 1993 15:29-36. Using such assemblies, it has been shown that osteoblast-like MC3T3 cells form cell aggregates when grown on non-degradable microspheres and produce collagen fibrils in the matrix between microspheres (Klement et al. J. Cellular Biochem. 1993 51(3):252-256). Also, rat stromal cells cultured for 2 weeks on cytodex-3 beads formed aggregates, began synthesizing mineralized matrix and showed elevated expression of type I collagen and osteopontin (Qui et al. Tissue Engineering 1998 4(1):19-34). However, when microspheres with greater density than the surrounding medium are placed in a rotating bioreactor, centrifugal force induces heavier-than-water microspheres to move outward and collide with the bioreactor wall. These collisions induce cell damage and are a confounding variable in tissue engineering.

In the present invention, lighter than or light as water, biocompatible, biodegradable microcarriers and scaffolds comprising these microcarriers are used in a three-dimensional culturing method for the growth of mineralized tissues in vitro in a rotating bioreactor. The combination of three-dimensionality and fluid flow of the present invention circumvents limitations associated with static three-dimensional culturing methods, eliminates confounding wall collisions, and increases the rate and extent of mineralized tissue formation in the rotating bioreactor. Scaffolds prepared in accordance with the present invention exhibit controllable and quantifiable motion in a bioreactor environment, thereby enhancing fluid transport throughout the scaffold. As demonstrated herein, scaffolds produced in accordance with the present invention support cell attachment, growth, and phenotypic expression over short-term culture ultimately resulting in enhanced synthesis of mineralized bone graft quality tissue.

SUMMARY OF THE INVENTION

An object of the present invention is to provide scaffolds for tissue engineering comprising biocompatible, biodegradable polymer-based, lighter than or light as water microcarriers. In a preferred embodiment, the scaffolds are seeded with cells via culturing in vitro in a rotating bioreactor.

Another object of the present invention is to provide a method of producing scaffolds for tissue engineering which comprises preparing biocompatible, biodegradable polymer-based microcarriers which are lighter than or light as water; bonding the biocompatible, biodegradable polymer-based microcarriers into a scaffold and seeding the scaffold with cell via culturing in vitro in a rotating bioreactor.

Another object of the present invention is to provide methods for using scaffolds comprising biocompatible, biodegradable polymer-based, lighter than or light as water microcarriers seeded with cells via culturing in vitro in a rotating bioreactor as tissue engineering devices. Scaffolds of the present invention can be seeded with cells including, but not limited to, osteoblast and osteoblast-like cells, endocrine cells, fibroblasts, endothelial cells, genitourinary cells, lymphatic vessel cells, pancreatic islet cells, hepatocytes, muscle cells, intestinal cells, kidney cells, blood vessel cells, thyroid cells, parathyroid cells, cells of the adrenal-hypothalamic pituitary axis, bile duct cells, ovarian or testicular cells, salivary secretory cells, renal cells, chondrocytes, epithelial cells, nerve cells and progenitor cells such as myoblast or stem cells, particularly pluripotent stem cells, and used in the regeneration of tissues derived from such cells.

DETAILED DESCRIPTION OF THE INVENTION

The present invention relates to tissue engineering scaffolds and methods for production of tissue engineering scaffold which promote growth in vitro of mineralized bone tissue in a rotating bioreactor. To produce these scaffolds, polymer microencapsulation methods were adapted for the formation of hollow, lighter than or light as water microcarriers of biocompatible, biodegradable polymers. Scaffolds were then fabricated by sintering together the lighter than or light as water microcarriers into a fully interconnected, three dimensional network. The microcarriers and scaffolds of the present invention move within the fluid medium of the rotating bioreactor in a near circular trajectory while avoiding collision with the bioreactor wall. Cell culture studies on the scaffolds of the present invention show that cells readily attach to microcarrier scaffolds. In addition, cells cultured in vitro in a rotating bioreactor on these lighter-than-water scaffolds retained their phenotype and showed significant increases in alkaline phosphatase expression and alizarin red staining by day 7 as compared to statically cultured controls.

By "lighter than or light as water microcarriers" it is meant microcarriers with a density equal to or less than water.

It has been shown previously that when osteoblast cells are co-inoculated with microcarriers in a rotating bioreactor a random aggregation occurs generated by the adherence of cells to microcarrier beads and the formation of cellular bridges between adjacent microcarriers (Granet et al. Cell Eng. 1998 36(4):513-519; Qiu et al. Tissue Engineering 1998 4(1):19-34; and Watts et al. Critical Reviews in Therapeutic Drug Carrier Systems 1990 7(3):235-259). However, this random aggregation that occurs in the rotating bioreactor is not conducive to strict quantitative comparison, because the size and shape of cell-bead aggregates as well as the degree of aggregation varies greatly. Such a limitation is overcome by the present invention via the sintered pre-assembly of microcarriers into dimensionally reproducible cell scaffolds prior to culture in the bioreactor. Furthermore, the microcarrier sintering method of the present invention is not limited by the adverse effects associated with the particulate leaching and consequently no unwanted degradation of the scaffold occurs during fabrication.

Microcarriers of the present invention which are light than or light as water exhibit buoyancy after immersion in deionized water, phosphate buffer solution and tissue culture medium. In a preferred embodiment, microcarriers of the present invention are fabricated to produce lighter than water densities from about 0.6 to about 0.99 g/cc as estimated using a density gradient column (ASTM D-1505). Microcarriers with densities as light as water or 1.0 g/cc can also be used. Using PLAGA to produce microcarriers of the present, the majority of lighter than or light as water microcarriers (47%) were within the range of 500 to 860 µm in diameter, with 19% from 300-500 µm, 8% at 100-300 µm and 2% less than 100 µm. Though 29% of microcarriers were greater than 860 µm in diameter, it is preferred that only microcarriers 860 µm and below are used for scaffold fabrication. For bone tissue engineering devices, it is preferred that microcarriers in the size range of 500-860 µm be used for scaffold fabrication, as they form structures with an expected pore size range of 113 to 356 µm shown to be suitable for osteoblast adherence and migration (Ishaug-Riley et al. Biomaterials 1998 19(15):1405-1412; Laurencin et al. Bone 1996 19(1):S93-S99). PLAGA microcarriers of this size range, when sintered, produce an interconnected network with an average pore size of 187 µm and aggregate density of 0.65 g/cc.

While PLAGA has been used as the exemplary microcarrier, as will be understood by those of skill in the art upon this disclosure, other biocompatible, biodegradable polymers can be used in the production of scaffolds of the present invention. Examples of such polymers include, but are not limited to, lactic acid polymers such as poly(L-lactic acid (PLLA), poly(DL-lactic acid (PLA), and poly(DL-lactic-co-glycolic acid) (PLGA). Blends of PLLA with PLGA, can also be used for these scaffolds. Other exemplary biodegradable polymers useful in the scaffolds of the present invention include, but are not limited to, polyorthoesters, polyanhydrides, polyphosphazenes, polycaprolactones, polyhydroxybutyrates, degradable polyurethanes, polyanhydrideco-imides, polypropylene fumarates, and polydiaxonane.

The hollow microcarriers are then fabricated into scaffolds, preferably via sintering in a mold for tissue engineering devices at a temperature which promotes bonding of the microcarriers but is below the melting temperature of the polymer. For example, PLAGA microcarriers were fabricated into 4 mm×2.5 mm cylindrical scaffolds by sintering at 60° C.

At this temperature, amorphous polymer chains of adjacent microcarriers move past one another and inter-lock forming a mechanical bond. Because this temperature is well below the melting temperature, however, collapse of individual microcarriers is avoided, thereby preserving their hollow, spherical geometry and the lighter-than-water density of the aggregate structure. Porosity is a result of the imperfect packing of spherical microcarriers inside the mold, and thus geometry dictates that there are no isolated spaces (pores) within the structure and that the network of pores in the scaffold is fully interconnected. The effect of sintering on the connectivity of microspheres was evident from SEM linkages showing two or more microspheres fused together at the contact regions. Assuming the spheres approach a close packed configuration in the mold, the diameter of the scaffold pores can be represented as interstitial voids in the structure. Again, geometry dictates that the pore of the structure is given by 0.225R in the case of a tetrahedral site (a void surrounded by 4 spheres in the shape of regular tetrahedron) or 0.414R in an octahedral, site (a void surrounded by 6 spheres in the shape of an octagon), where R is the radius of the surrounding spheres.

The porosity and pore size distribution of typical microcarrier scaffolds was measured using mercury porosimetry. Although the broad distribution of microcarrier size likely decreases the resulting pore diameter and increases packing efficiency, the measured porosity of 31% slightly exceeds that of close packing (26%). The average pore size distribution of 12 microcarrier scaffolds where the median pore is 187 µm is well within the theoretical expectation for close packed spheres. Although the value median pore diameter exceeds the minimum requirement for cell ingrowth and migration (Ishaug et al. J. Biomed. Mater. Res. 1997 36(1):17-28; Ishaug-Riley et al. Biomaterials 1998 19(15):1405-1412; Goldstein et al. Tissue Engineering 1999 5(5):421-433; Laurencin et al. Bone 1996 19(1):S93-S99), the level of total pore volume or porosity of microcarrier scaffolds is 50-60% less than that of similar polymeric matrices proposed for bone repair (Ishaug et al. J. Biomed. Mater. Res. 1997 36(1):17-28; Ishaug-Riley et al. Biomaterials 1998 19(15):1405-1412; Goldstein et al. Tissue Engineering 1999 5(5):421-433).

The motion of microcarrier scaffolds constructed primarily from 500 to 860 µm lighter than or light as water microcarriers and fashioned into 4×2.5 mm cylindrical discs within the rotating bioreactor was assessed. Particle tracking analysis revealed an instantaneous velocity of 98 mm/second and a trajectory completely absent of wall collisions once equilibrium motion was reached.

Cell attachment to microcarrier scaffolds during rotating culture was estimated from cell concentration profiles taken at times 4, 8, 12, and 24 hours following co-inoculation with lighter than or light as water scaffolds. Cells used in these experiments were osteoblast-like cells. As will be understood by those of skill in the art upon reading this disclosure, however, the scaffolds of the present invention can actually be seeded with any cell type which exhibits attachment and ingrowth and is suitable for the intended purpose of the scaffold. Some exemplary cell types which can be seeded into these scaffolds include, but are not limited to, osteoblast and osteoblast-like cells, endocrine cells, fibroblasts, endothelial cells, genitourinary cells, lymphatic vessel cells, pancreatic islet cells, hepatocytes, muscle cells, intestinal cells, kidney cells, blood vessel cells, thyroid cells, parathyroid cells, cells of the adrenal-hypothalamic pituitary axis, bile duct cells, ovarian or testicular cells, salivary secretory cells, renal cells, chondrocytes, epithelial cells, nerve cells and progenitor cells such as myoblast or stem cells, particularly pluripotent stem cells.

In experiments with osteoblast-like cells, cell density in the bioreactor medium decreased about 60%. The decreased concentration of suspended cells during culture is assumed to reflect the attachment of these cells to the scaffolds. By dividing the estimated quantity of attached cells by the total number of scaffolds present in culture, cell seeding was estimated to be approximately $1.4 \times 10^5$ cells/scaffold. After 24 hours of dynamic seeding, a sampling of 6 to 10 cell-scaffolds was used to measure directly the number of cells attached to scaffolds using fluorometric DNA analysis. Measurements of attached cell were in excellent agreement with cell concentration estimates with an average value of $1.3 \times 10^5$ cells per scaffold and standard deviation of $2.0 \times 10^4$ cells. The average surface area per scaffold was calculated to be approximately 2 $cm^2$ resulting in a cell seeding density of approximately $6.5 \times 10^4$ cells/$cm^2$.

Cell proliferation was examined on lighter than or light as water microcarrier scaffolds over a period of 7 days with cell numbers measured immediately following cell seeding and at days 3 and 7. Cells cultured on lighter than or light as water scaffolds in the rotating bioreactor show evidence of a lower rate and extent of proliferation than those cultured on non-rotating controls. Significant differences in cell numbers could be detected by day 7 ($p<0.05$). The presence of cells within the pores of the scaffold that nearly cover the entire surface of the internal microcarriers was verified by SEM. By progressively focusing the microscope down the pore of the structure, it was estimated that cells had penetrated as deep as 800 µm.

The retention of osteoblastic phenotype was evaluated by ALP histochemical staining and calorimetric analysis. Cells were stained for ALP expression on lighter than or light as water scaffolds in the rotating bioreactor and on the non-rotating three-dimensional controls at days 3 and 7. Positive ALP staining is evident at each time point and for each culture condition. At each time point, more cells per unit area are present on scaffolds cultured under non-rotating three-dimensional conditions than those cultured in the rotating bioreactor, which is consistent with fluorometric DNA analysis described herein. Calorimetric analysis was also performed at 24 hours and at day 7. These results were normalized by the actual number of cells present in each scaffold. It was found that by day 7 the actual amount of ALP expressed per cell is significantly higher for cells cultured in the rotating bioreactor than on non-rotating three-dimensional controls ($p<0.05$).

The production of calcified matrix was analyzed by alizarin red histochemical staining. Scaffolds cultured in the rotating bioreactor showed substantially greater alizarin positive extracellular matrix material by day 7 as compared to three-dimensional controls ($p<0.05$). To quantify the amount of early stage calcified matrix formation, alizarin red staining techniques were adapted for calorimetric analysis by solubilizing the red matrix precipitate with cetyl pyridinium chloride to yield a purple solution suitable for optical density measurements at 562 nm. Quantities of ALZ stained matrix were expressed as a molar equivalent $CaCl_2$ concentration and normalized by the average number of cells per scaffold as determined in companion proliferation studies. Significant increases in the quantity of ALZ stained matrix produced on lighter than or light as water scaffolds under rotating conditions at days 3 and 7 as compared to non-rotating controls were observed.

Thus, as demonstrated herein, lighter than or light as water polymer-based microcapsules are excellent cell microcarriers providing a low shear, non-turbulent flow environment for attached cells that avoids damaging collisions with the bioreactor wall. These scaffolds adopt a particle trajectory absent of confounding wall collisions, while maintaining a three-dimensional geometry open to mass transport of nutrients and waste products. In particular, the hydrodynamic flow environment produced by the motion of lighter than or light as water scaffolds in the rotating bioreactor enhances $O_2$ and nutrient transport to cells at the near surface (external) of the scaffold and possibly those in the scaffold interior (internal). This may act to advance phenotype development and tissue formation in the system of the present invention. Further, cell seeding of the scaffolds in the rotating bioreactor, as opposed to static seeding methods for these scaffolds, enhances cell migration to the interior of the scaffold and promotes homogeneity of initial cell seeding from one scaffold to another. Accordingly, the scaffolds of the present invention provide a combination of three-dimensionality and fluid transport in the absence of damaging wall collisions that appears to be a closer approximation of the in vivo environment of the cell thereby expanding capacity for ex vivo tissue synthesis.

Scaffolds of the present invention are expected to particularly useful in developing bone graft quality tissue. However, as will be understood by one of skill in the art upon reading this disclosure, the method of Scaffolds of the present invention are expected to particularly useful in developing bone graft quality tissue. However, as will be understood by one of skill in the art upon reading this disclosure, the method of scaffold fabrication disclosed herein can be used to generate a variety of microcarrier scaffolds of different component size ranges, associated three-dimensional architecture, and density useful in a variety of tissue engineering applications. Scaffolds seeded with cells including, but not limited to, osteoblast and osteoblast-like cells, endocrine cells, fibroblasts, endothelial cells, genitourinary cells, lymphatic vessel cells, pancreatic islet cells, hepatocytes, muscle cells, intestinal cells, kidney cells, blood vessel cells, thyroid cells, parathyroid cells, cells of the adrenal-hypothalamic pituitary axis, bile duct cells, ovarian or testicular cells, salivary secretory cells, renal cells, chondrocytes, epithelial cells, nerve cells and progenitor cells such as myoblast or stem cells, particularly pluripotent stem cells, are useful in the regeneration of tissues derived from such cells.

The following nonlimiting examples are provided to further illustrate the present invention.

EXAMPLES

Example 1

Buoyant Microcarrier Fabrication

A conventional microsphere fabrication technique was adapted for the formation of hollow, lighter than or light as water microcarriers of bioerodible poly(d,l-lactic-co-glycolide) copolymer. For this technique, a 25% w/v polymer solution of 50:50 PLAGA (molecular weight approximately 30,000) was dissolved in methylene chloride, and poured slowly into a 1000 ml beaker containing 0.1% PVA (Polysciences, Lot #413322, molecular weight 25,000). The solution was stirred continuously (Caframo, Model BDCISSO) at 1000 rpm for 4 to 6 hours to allow for solvent evaporation. Buoyant microcarriers were harvested by vacuum filtration (Whatman, 54 µm), washed with deionized water, and lyophilized (Lyph-lock 12, Labconco Corp.) for 24 hours. Size distribution was determined by mechanically sifting the microcarriers using a series of stainless steel sieves with selected mesh sizes. Microcarriers were freeze fractured and analyzed with scanning electron microscopy to confirm that the carriers were indeed hollow. In vitro buoyancy was verified over 7 days by immersion inside a water-tight container maintained at 37° C. in an oscillating (60 opm) water bath.

Example 2

Scaffold Fabrication and Characterization

Microcapsules of a selected size range and weight were poured into a stainless steel mold and heated in an oven (Precision Gravity Convection Incubator) for 1 hour at 60° C., several degrees above the glass transition temperature for the PLAGA 50:50 ($T_g$=45-50° C.). Microcarriers bonded to each other while maintaining their hollow, spherical geometry. Scaffolds used for bioreactor culture were exposed to ultraviolet irradiation for 30 minutes on each side in an effort to minimize bacterial contamination. Microcarrier scaffolds were characterized using a low field emission scanning electron microscope (SEM, JEOL 6300). For SEM, specimens were coated with gold and examined for pore inter-connectivity, degree of microcarrier bonding, and deformation of microcarriers. The porosity of the structure was measured by porosimetry using the Micromeritics Autopore HI porosimeter. Specifically, cylindrical polymer scaffolds, 4 mm in diameter and approximately 2.5 mm in length were placed in a 5 cc penetrometer, subjected to a vacuum of 50 µm Hg, and infused with mercury. Porosity is determined by measuring the volume of the mercury infused. In addition to an overall percentage of porosity for the polymer scaffold, porosimetry will also give an approximate distribution of pore sizes within the polymer scaffold, allowing for more accurate characterization of the scaffold geometry.

Example 3

Numerical Model Simulation and Particle Motion Analysis

The equations of motion governing microcarrier motion in the rotating bioreactor are as follows. For the particle position (x, y) and velocity ($v_x$, $v_y$), microcapsule motion relative to the rotating fluid is governed by equations:

$$\frac{dx}{dt} = v_x \tag{1}$$

$$\frac{dv_x}{dt} = -\frac{1}{\rho_{part} \cdot V_{part}}$$

$$\left[ \begin{array}{c} p \cdot S \cdot C_d \cdot v_x + (\rho_{part} - \rho_{fluid}) \cdot V_{part} \cdot \omega^2 \cdot x + \\ 2 \cdot (\rho_{part} - \rho_{fluid}) \cdot V_{part} \cdot \omega \cdot x - (\rho_{part} - \rho_{fluid}) \cdot V_{part} \cdot g \cdot \sin(\omega t) \end{array} \right]$$

$$\frac{dy}{dt} = v_y$$

$$\frac{dv_y}{dt} = -\frac{1}{\rho_{part} \cdot V_{part}}$$

$$\left[ \begin{array}{c} p \cdot S \cdot C_d \cdot v_y + (\rho_{part} - \rho_{fluid}) \cdot V_{part} \cdot \omega^2 \cdot y - \\ 2 \cdot (\rho_{part} - \rho_{fluid}) \cdot V_{part} \cdot \omega \cdot y - (\rho_{part} - \rho_{fluid}) \cdot V_{part} \cdot g \cdot \cos(\omega t) \end{array} \right]$$

$$S = \pi \cdot R_{part}^2$$

$$C_d = \frac{24}{Re} + \frac{6.0}{1.0 + \sqrt{Re}} + 0.4$$

where ($\rho_{sphere} - \rho_{fluid}$) is the difference between the density of the microcapsule and surrounding fluid, Re is the Reynolds number, $V_{part}$ is the microcarrier volume, $C_d$ is the drag coefficient at $Re<2\times10^5$, p is the stagnation pressure, S is the microcapsule planar surface area, and Z is the axis of rotation. A numerical solution to these equations was obtained by way of a fourth order Runga Kutta integration scheme run on a local workstation, using an adaptive stepwise control algorithm to ensure convergence through the integration period and assuming a specific starting position (x,y) within the bioreactor. Using this numerical model, scaffold parameters (e.g. density and drag coefficient) have been identified which yield particle trajectories without any confounding wall collisions. Scaffolds were then fabricated from component microcarriers which meet these design criteria.

A particle tracking system built for the rotating bioreactor was used to compare resulting scaffold motion in the rotating bioreactor relative to the culture medium. The particle tracking system is comprised of a rotating CCD camera (Cohu, Inc.) that is in synchrony with a rotating High Aspect Ratio Vessel (HARV). Particle motions are videotaped (Sony SVO-9500 MD) and digitally re-recorded using a Sony Frame Code Generator and frame grabber (Media Cydernetics). Image analysis is carried out using Image Pro (Phase 3 Imaging, Inc.). Lighter-than-water PLAGA microcarriers and microcarrier scaffolds were incubated in distilled water at room temperature for 24 hours in a non-rotating bioreactor vessel and their trajectories recorded during bioreactor rotation using the tracking apparatus. A temporal description of scaffold trajectory was measured over consecutive frames from which particle velocities were computed. From these velocity measurements and based on the geometry of the scaffolds (and diameter of isolated microcarriers), maximum fluid shear stress is estimated by assuming uniform flow past a single microcarrier and using the stokes equation:

$$\sigma = \frac{-3\mu U}{2a} \quad (2)$$

where $\sigma$ is shear stress, $\mu$ is viscosity, U is flow velocity and a is the diameter of the microcarrier.

Example 4

Cell Seeding and Culture

The human SaOS-2 line (ATCC A HTB-85), which exhibits homogeneous and reproducible expression of cellular alkaline phosphatase over an infinite life span was used. For all experiments, cells were maintained in M199 (Gibco) culture medium supplemented with 10% fetal bovine serum (Sigma), 2.5 mM L-glutamine and 3 mM b-glycerol phosphate. SaOS-2 cells were grown to confluency and digested in 0.01% trypsin in 0.04% EDTA (Gibco) for 10 minutes. Cells were then resuspended in a minimal amount of media, their numbers determined with a Coulter Counter, and diluted to an appropriate cell density. Prior to cell seeding, PLAGA scaffolds (n=36) were washed in phosphate buffered saline (PBS), and placed inside a single bioreactor vessel (Synthecon) filled with 55 ml of complete medium containing no cells. After 10 minutes, the bioreactor vessel was inoculated with $8\times10^6$ cells and mounted onto a multi-HARV rotating unit turning at 25 rpm. Cell attachment to microcarrier scaffolds in the rotating vessel was estimated from the decrease of cell density in the supernatant fluid observed over 24 hours. At time intervals 4, 8, and 12 hours, 0.5 ml of the cell suspension was removed from the bioreactor, re-suspended in trypsin solution to dissociate cell aggregates and cell numbers were determined using a coulter counter. At 24 hours, the entire cell suspension was removed and the cell number determined.

Example 5

Cell Counting

Immediately following the seeding of the cells for an experiment, a random sampling (n=6 to 10) of selected scaffolds was removed and the initial number of attached cells were determined by means of a fluorometric DNA assay as described by Labarca and Paigen (Anal. Biochem. 1980 102: 344-352). The remaining scaffolds were washed with PBS and divided equally into two experimental groups. Each group of scaffolds was placed, respectively, into two new bioreactor vessels and re-fed with 55 ml of fresh culture medium. To determine the effect of culture vessel rotation on cell function, one vessel was mounted onto a multi-HARV unit and rotated at 25 rpm and the other was cultured statically (no-rotation) as a control. Each vessel was cultured at 37° C. and 5% $CO_2$ for 7 days. At days 3 and 7, additional scaffolds were removed for DNA quantification. Scaffolds used for DNA analysis were washed 3 times in PBS, combined with 3 ml of additional PBS containing 2 mM EDTA, and pulverized using a tissue homogenizer (PowerGen 35, Fisher) with a 10 mm diameter saw-tooth generator for 1 minute. Cells were ruptured by 2 minutes of further homogenization at 30,000 rpm with a 5 mm diameter flat bottom generator. Homogenates were frozen at −70° C. until the day of analysis. On the day of analysis, 1 ml of scaffold homogenate was combined with 7 μl of a 200 μg/ml solution of bisbenzimide H33258 dye (Calbiochem) and vortexed vigorously. Fluorescence was read using a Tecan Spectrofluor microplate reader with an emission wavelength of 465 nm and an excitation wavelength of 360 nm. Cell standards were used to convert measured fluorescence to cell numbers, and unseeded but cultured scaffolds were analyzed to determine any effect of PLAGA autofluorescence.

Example 6

Alkaline Phosphatase Activity

Alkaline Phosphatase (ALP) activity was measured by using adaptations of standard histochemical (Van Belle, H. Biochimica et Biophysics Acta 1972 289:158-168) and colorimetric (Rattner et al. In Vitro Cellular & Developmental Biology—Animal 1997 33(10):757-762) methods. At days 3 and 7, scaffolds were removed from both the rotating and non-rotating bioreactor vessels and washed two times with PBS. Scaffolds were then incubated for 30 minutes at 37° C. with Napthol AS-BI (Sigma, N-2250) phosphate salt (0.5 mg/ml; Sigma) and N,N-Dimethyl Formamide (10 μg/ml; Sigma D-8654) in 50 mM Tris buffer (pH 9.0), in the presence of Fast Red (Sigma, F-2768) violet salt (1.0 mg/ml). After 30 minutes, cells were washed two times with PBS and fixed by incubation in 2% paraformaldehyde for 30 minutes at 4° C. ALP staining was viewed by light 5 microscopy. Scaffolds were fractured into halves in order to visualize cells in the interior regions of the 3-dimensional structure.

In addition, ALP expression was quantified in each of the cell-scaffold homogenates used for fluorometric DNA analysis. For this analysis, aliquots of cell homogenates were incubated at 37° C. for 30 minutes in 0.1 M $Na_2CO_3$ buffer solution (pH 10) containing 2 mM $MgCl_2$ with disodium p-nitrophenyl phosphate (pNP-PO$_4$) as the substrate. Standard solutions were prepared by serial dilutions of 0.5 mM p-nitrophenol (pNP) in Na$_2$CO$_3$ buffer. Enzymatic activity was expressed as total mmoles of pNP produced per minute per total cell number determined by fluorometric DNA analysis. Absorbance was measured at 415 nm using a Tecan Spectrofluor microplate reader.

Example 7

Alizarin Red Calcium Quantification

The effectiveness of sodium 1,2-dihydroxy anthraquinone-3-sulfonate, commonly known as Alizarin Red (ALZ), as a chelating compound and colorometric reagent for spectrophotometric determination of calcium is well established (Wu, L. and Forsling, W. Acta Chemica Scandinavica 1992 46:418-422). ALZ spectrophotometric methods were adapted for the determination of mineralized matrix production (Stanford et al. J. Biol. Chem. 1995 270:9420-9428) on lighter than or light as water PLAGA by osteoblast-like cells. Scaffolds were removed from the bioreactor, washed in ddH$_2$O, and incubated in 40 mM Alizarin red solution (pH 4.2) for 10 minutes at room temperature. To remove unreacted ALZ, scaffolds were washed 5-10 times in ddH$_2$O (until water was clear). Scaffolds were then incubated in 10% cetyl pyridinium chloride for 15 minutes to solubilize reacted ALZ and pulverized using a tissue homogenizer (PowerGen 35, Fisher) with a 10 mm diameter saw-tooth generator. Serial dilutions of 1 N CaCl$_2$ were used as standards. ALZ concentration per cell was calculated as molar equivalent CaCl$_2$ divided by the average cell number at each time point as determined by fluorometric DNA analysis. Absorbance was measured at 570 nm using a Tecan Spectrofluor microplate reader.

Example 8

Scanning Electron Microscopy

Before seeding with cells, microcarriers and microcarrier scaffolds were coated with gold and visualized using a low field emission electron microscope (JEOL 6300) at 2 keV accelerating voltage. To evaluate cell attachment and morphology to lighter-than-water scaffolds cultured in the bioreactor, scaffolds were cultured as described above and removed at day 7 for SEM analysis. Attached cells were fixed to scaffold substrates by washing thoroughly with PBS, then incubation in 1% and 3% glutaraldehyde for 1 hour and 24 hours, respectively. Following fixation, cells were washed with PBS, placed through a series of graded ethanol dehydrations and allowed to air dry. Finally, cell-scaffolds were coated with carbon and analyzed at 2 keV.

Example 9

Statistical Analysis

Statistical analysis was performed using JMP IN 3.2.1 software. One-way ANOVA was performed to determine any statistically significant relationship between the rotating and non-rotating conditions with respect to the quantity of reacted ALZ, ALP expression, and cell number. Statistical significance was attained at p<0.05. Three scaffolds were analyzed at each time point and for each quantitative assay.

What is claimed is:

1. A scaffold for tissue engineering comprising a 3-dimensional network of microcarriers, said microcarriers comprising at least one biocompatible, biodegradable organic polymer and individually presenting an organic polymer surface to adjacent microcarriers and having densities less than or equal to that of water, wherein adjacent microcarriers are fused to one another at an interface, each interface comprising a region of direct polymer-polymer contact, and wherein the 3-dimensional network of microcarriers further comprises a network of interconnected pores.

2. The scaffold of claim 1 further comprising cells.

3. The scaffold of claim 2 wherein the cells comprise osteoblast cells or cells exhibiting an osteoblastic phenotype, endocrine cells, fibroblasts, endothelial cells, genitourinary cells, lymphatic vessel cells, pancreatic islet cells, hepatocytes, muscle cells, intestinal cells, kidney cells, blood vessel cells, thyroid cells, parathyroid cells, cells of the adrenal-hypothalamic pituitary axis, bile duct cells, ovarian or testicular cells, salivary secretory cells, renal cells, chondrocytes, epithelial cells, nerve cells or progenitor cells.

4. The scaffold of claim 1 wherein the microcarriers are hollow.

5. The scaffold of claim 1 wherein the network of interconnected pores defines a scaffold porosity, and said porosity is 31% of the total volume of the scaffold.

6. The scaffold of claim 1 wherein the network of interconnected pores is characterized by a pore size, and the pore size of the scaffold is in the range of from 113 to 356 microns.

7. The scaffold of claim 1 wherein the biocompatible, biodegradable polymer comprises a polylactic acid, a polyorthoester, a polyanhydride, a polyphosphazene, a polycaprolactone, a polyhydroxybutyrate, a degradable polyurethane, a polyanhydrideco-imide, a polypropylene fumarate, or a polydiaxonane, or a copolymer or mixture thereof.

8. The scaffold of claim 1 wherein the biocompatible, biodegradable polymer is a polylactic acid polymer or a polylactic acid/polyglycolic acid copolymer or mixture thereof.

9. The scaffold of claim 1 wherein the microcarriers are microspheres and the diameter of the microspheres is in the range of 100 to 860 microns.

10. The scaffold of claim 1 wherein the microcarriers are microspheres and the diameter of the microspheres is in the range of 100 to 500 microns.

11. The scaffold of claim 1 wherein the microcarriers are microspheres and the diameter of the microspheres is in the range of 300 to 500 microns.

12. The scaffold of claim 1 wherein the microcarriers have a density in the range of 0.6 to 0.99 gram per cubic centimeter.

13. The scaffold of claim 2 wherein the cells are attached to the scaffold by seeding, said seeding being achieved via culturing in vitro in a rotating bioreactor.

14. The scaffold of claim 3 wherein the cells comprise osteoblast cells, cells exhibiting an osteoblastic phenotype, or progenitor cells or mixtures thereof.

15. A method for producing the scaffold of claim 1 comprising:
(a) preparing microcarriers comprising at least one biocompatible, biodegradable organic polymer and presenting an organic polymer surface and which have densities less than or equal to that of water;
(b) organizing the microcarriers so that the polymer surfaces of adjacent microcarriers contact one another; and
(c) bonding the biocompatible, biodegradable polymer-based microcarriers into a scaffold, such that the bonding occurs directly between the organic polymer surfaces of adjacent microcarriers.

16. The method of claim 15 wherein the bonding is achieved by a process comprising heating the microcarriers at a temperature above the glass transition temperature but below the melting temperature of the biocompatible, biodegradable polymers.

17. A method for regenerating a selected tissue comprising seeding the scaffold of claim 1 with cells which generate the selected tissue and culturing the scaffold and seeded cells in a rotating bioreactor.

18. The method of claim 17 wherein the seed cells comprise seed cells comprise osteoblast and osteoblast-like cells, endocrine cells, fibroblasts, endothelial cells, genitourinary cells, lymphatic vessel cells, pancreatic islet cells, hepatocytes, muscle cells, intestinal cells, kidney cells, blood vessel cells, thyroid cells, parathyroid cells, cells of the adrenal-hypothalamic pituitary axis, bile duct cells, ovarian or testicular cells, salivary secretory cells, renal cells, chondrocytes, epithelial cells, nerve cells or progenitor cells.

19. The method of claim 17 wherein the scaffold in the rotating bioreactor moves within the rotating bioreactor in a near circular particle trajectory.

* * * * *